US006280925B1

(12) United States Patent
Brockbank

(10) Patent No.: US 6,280,925 B1
(45) Date of Patent: Aug. 28, 2001

(54) POLYETHYLENE GLYCOL AND GLUTATHIONE COMPOSITION AND METHOD FOR THE TREATMENT OF BLOOD VESSELS PRIOR TO CRYOPRESERVATION

(75) Inventor: Kelvin G. M. Brockbank, Charleston, SC (US)

(73) Assignee: Organ Recovery Systems, Inc., Des Plaines, IL (US)

(*) Notice: Subject to any disclaimer, the term of this patent is extended or adjusted under 35 U.S.C. 154(b) by 0 days.

(21) Appl. No.: 09/499,520

(22) Filed: Feb. 10, 2000

Related U.S. Application Data
(60) Provisional application No. 60/119,798, filed on Feb. 11, 1999.

(51) Int. Cl.$^7$ ............................................... A01N 1/02
(52) U.S. Cl. ............................. 435/2; 435/325; 436/18
(58) Field of Search ........................... 435/2, 325; 436/18

(56) References Cited

U.S. PATENT DOCUMENTS

| | | | |
|---|---|---|---|
| 4,938,961 | 7/1990 | Collins et al. | 424/606 |
| 5,599,659 | * 2/1997 | Brasile et al. | 435/1.1 |
| 5,834,509 | * 11/1998 | Malfroy-Camine et al. | 514/492 |
| 6,007,978 | * 12/1999 | Goodrich et al. | 435/2 |
| 6,127,181 | * 10/2000 | Kadkade | 435/420 |

FOREIGN PATENT DOCUMENTS

WO 01/01774
A1  1/2001  (WO).

OTHER PUBLICATIONS

Collins et al (II), Lancet, vol. 338, pp. 890–891, Oct. 1991.*
O'Neil et al, Crylbioligy; vol. 34, pp. 295–301, 1997.*
Bryan et an, Chest, vol. 100, pp. 1694–1702 (abstract), Dec. 1991.*
Ohboshi et al, Anim, Reprod. Sci., vol. 48, pp. 27–36 (abstract), Jul. 1997.*
Davies et al, Eur. J. Vasc. Endovasc. Surg., vol. 17, pp. 493–500 (abstract), Jun. 1999.*
K. Murad, et al., "Molecular Camouflage of Antigenic Determination on Intact Mammalian Cells: Possible Applications to Transfusion Medicine," *Blood* 88 (Supplement 1) 1765, p. 444a (1996).

A. Collins, et al., "Heart preservation solution containing polyethyleneglycol: an immunosuppressive effect?," *The Lancet* 338, pp. 890–891 (1991).
D. Deaton, et al., "Evaluation of cryopreserved allograft venous conduits in dogs," *The Journal of Thoracic and Cardiovascular Surgery* 103, No. 1, pp. 153–162 (1992).
M. Davies, et al., "Functional and Histological Differences in Autogenous and Allogenic Vein Grafts: Two Different Vasculopathies?," *Journal of Surgical Research* 69, Article No.JR975019, pp. 14–22 (1997).
M. Scott, et al., *The Other Blood Substitute: Antigenically Inert Erythrocytes*, pp. 133–150.
M. Schlafer, "Pharmacological Considerations in Cryopreservation," *Organ Preservation for Transplantation (2$^{nd}$ Edition)*, Marcel Dekker, Inc., New York, pp. 177–212 (1984).
J.M. Malone, et al., "Venous Cryopreservation: Endothelial Fibrinolytic Activity and Histology," *Journal of Surgical Research* 29, pp. 209–222 (1980).
Y. Tokunaga, et al., "The Immunosuppressive Effect of Polyethylene Glycol In A Flush Solution For Rat Liver Transplantation," *Transplantation* 54, No. 4, pp. 756–758 (1992).
D. Showalter, et al., "Cryopreserved venous homografts as vascular conduits in canine carotid arteries," *Surgery* 106, No. 4, pp. 652–659 (1989).
N. Augelli, et al., "Allograft Vein Patency In A Canine Model," *Transplantation* 52, No. 3, pp. 446–470 (1991).
J. Elmore, et al., "Functional changes in canine saphenous veins after cryopreservation," *International Angiology* 11, No. 1, pp. 26–35 (1992).
H. Bank, et al, "Transplantation of Cryopreserved Canine Venous Allografts," *Journal of Surgical Research* 50, pp. 57–66 (1991).

* cited by examiner

Primary Examiner—James H. Reamer
(74) Attorney, Agent, or Firm—Oliff & Berridge, PLC

(57) ABSTRACT

A composition including polyethylene glycol (PEG) and glutathione (GSH), is used to treat vascular grafts prior to cryopreservation. The PEG and GSH containing composition is use to treat vascular tissue grafts prior to their cryopreservation to ameliorate the onset of intimal hyperplasia. The composition can also be used to treat vascular tissue grafts prior to cryopreservation by incorporation into solutions used for vascular tissue graft transport and/or in other vascular tissue graft processing steps.

30 Claims, 4 Drawing Sheets

POLYETHYLENE GLYCOL AND GLUTATHIONE COMPOSITION AND METHOD FOR THE TREATMENT OF BLOOD VESSELS PRIOR TO CRYOPRESERVATION

This application claim benefit to Provisional Application No. 60/119,798 Feb. 11, 1999.

FIELD OF INVENTION

This invention relates to the field of blood vessel and vascularized organ grafts, and more particularly, to a composition and methods for use of the composition in the treatment of vascular graft segments prior to cryopreservation, storage and transplantation.

BACKGROUND

Autogenous veins or arteries are the most common and most preferred conduits in revascularization of coronary and peripheral occlusive vascular disease. With the increasing age of the population and the increasing number of redo operations due to the development of intimal hyperplasia (an increase in the size of a tissue or organ due to an increase in the number of component cells) and accelerated atherosclerosis (obstruction of the arteries by localized fatty deposits) in bypass grafts, it is expected that over one third of patients will not have one or both of these conduits available at the time of revascularization. Prosthetic materials can be used for large diameter vessels; however their patency (state of being open or unblocked) is poor when used as conduits to replace small diameter vessels. There is, therefore, a need for alternative conduits, particularly for smaller diameter vessels. Cryopreserved arterial and venous allografts have been suggested as a possible "off-the-shelf" solution for small diameter vessel bypass. Clinical studies of these gmfts have been limited in both coronary and peripheral circulation, but demonstrate the significant stigma of poor patency irrespective of position.

Blood vessels are also a ubiquitous component of human vascularized tissues and organs, which may, one day, be successfully stored by cryopreservation for transplantation. Furthermore, providing that significant immunological issues can be overcome, cryopreserved xenografts may, one day, provide an unlimited supply of vascularized tissues and organs for storage by cryopreservation.

Although not commonly employed, polyethylene glycol (PEG) has been reported to be a cryopreservation agent (see "Pharmcological Considerations in Cryopreservation" by Shlafer in Organ Preservation for Transplantation, Karow AM and Pegg DE (eds) Marcel Dekker, New York, pp 177–212 (1981)). It has also been suggested that PEG may reduce the immune response to allogeneic blood transfusions and transplants (see "Molecular Camouflage of Antigenic Determinants on Intact Mammalian Cells: Possible Applications to Transfusion Medicine" by Murad et al. in Blood 88 (Supplement 1): 1765 (1996); "The Other Blood Substitute: Antigenically Inert Erythrocytes" by Scott et al.; and "Heart Preservation Solution Containing Polyethylene Glycol: An Immunosuppressive Effect" by Collins et al. in Lancet, 338:390 (1991)). A 30% reduction has been observed in the incidence of acute rejection in a group of heart transplant recipients in which the donor organ had been stored at 4° C. in a solution containing 5%. In a subsequent study, PEG produced a modest but statistically significant increase in rat liver allograft survival time from 9.6 to 11.9 days (see "The Immunosuppressive Effect of Polyethylene Glycol in a Flush Solution for Rat Liver Transplantation" by Tokunaga et al. in Transplantation 54:756–8 (1992)). In these studies, the transplanted organ was merely soaked in the PEG solution without subsequent cryopreservation.

U.S. Pat. No. 4,938,961 to Collins et al. discloses an organ preservation solution containing polyethylene glycol, along with a variety of further ingredients including: 30–40mM NaOH, 100 mM Lactobionic acid, 25 mM KH2PO4, 10 mM KOH, 30 mM raffinose, and 3 mM glutathione. This solution is used for the transport of an organ from a donor to a recipient in cold solution.

In recent unpublished studies, it was found that the development of intimal hyperplasia in cryopreserved allografts is accelerated compared to fresh allografts due to the additional cryopreservation insults superimposed on the melee of other variables associated with the placement of veins into the arterial circulation.

Cryopreserved allografts have been shown to have extensive medial fibrosis, intnnal hyperplasia and a significant infiltrate consisting of activated macrophages, lymphocytes, granulocytes and plasma cells (see "Transplantation of Cryopreserved Canine Venous Allografts" by Bank et al. in J Surg Res 50:57–64 (1991), "Cryopreserved Venous Homografts as Vascular Conduits in Canine Carotid Arteries" by Showalter et al. in Surgery 106:652–659 (1989), "Evaluation of Cryopreserved Allograft Venous Conduits in Dogs" by Deaton et al. in J Thorac Cardiovasc Surg 103:153–162 (1992) and "A study of the Functional and Histological Differences in Autologous and Allogenic Vein Grafts-Two Different Vasculopathies" by Davies et al. in J Surg Res 69:14–22 (1997)).

SUMMARY OF THE INVENTION

According to the present invention, a new composition, which includes both polyethylene glycol (PEG) and an antioxidant, such as glutathione (GSH), may be used to treat vascular grafts prior to cryopreservation and transplantation to ameliorate the onset of intimal hyperplasia, which would otherwise occur after vascular graft cryopreservation and transplantation. The PEG and GSH containing composition may be incorporated into a transport or other processing solution employed for the vascular grafts prior to their cryopreservation. The vascular grafts are preferably contacted with the composition containing PEG and GSH for at least the 12 hours prior to cryopreservation.

DETAILED DESCRIPTION OF PREFERRED EMBODIMENTS

Figure 1:
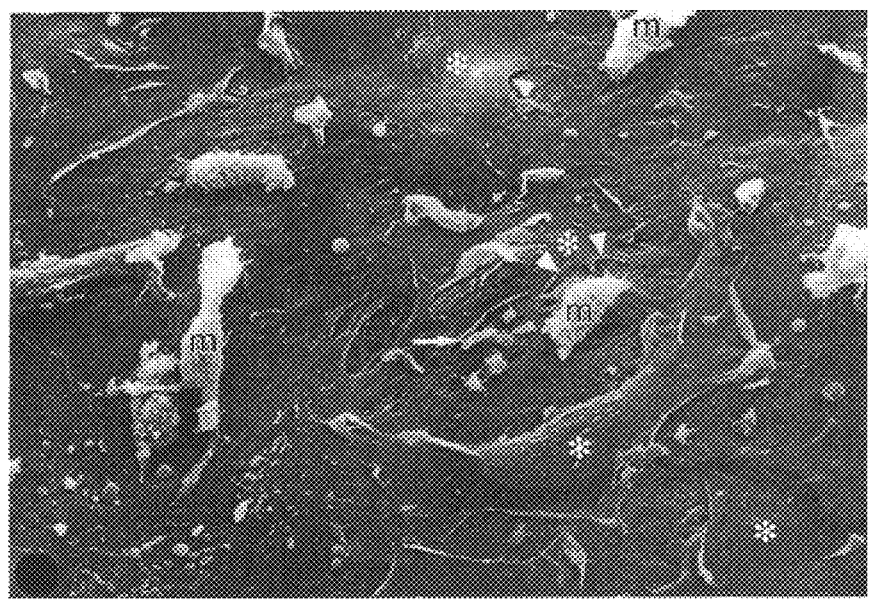
FIG. 1 is a scanning electron micrograph from a fresh allograft after 28 days showing spindle shaped cells.

A new composition, which includes polyethylene glycol (PEG) and an antioxidant, such as glutathione (GSH), may be used to treat vascular tissues prior to cryopreservation and transplantation. The PEG and GSH or other antioxidant containing composition is preferably incorporated into solutions employed for venous or other vascular tissues prior to cryopreservation of the tissues to ameliorate the onset of post-transplantation intimal hyperplasia, which would otherwise occur after cryopreservation of the vascular tissues.

In embodiments of the present invention, it is preferred that the polyethylene glycol have a weight average molecular weight of from about 1000 to about 24,000. More preferably, the polyethylene glycol has a weight average molecular weight of from about 12,000 to about 20,000 and even more preferably about 16,000.

Glutathione (OSH), α-glutomylcysteinylglycine, is an antioxidant peptide that contains glutamic acid, cysteine and glycine. Other antioxidant compounds will also be effective (i.e. Vitamins A, C and E, magnesium ascorbyl phosphate, retinol, catalase, superoxide dismutase, Allopurinol, and others).

In this application, the term "allograft" refers to biological material intended for trnplantation into another individual of the same species. "Autograft" refers to biological material intended for implantation into the individual from whom the material was recovered. "Xenograft" refers to biological material intended for transplantation between different species.

"Tissue engineering" refers to the development, design and implantation of devices composed of materials and living cells to replace defective or diseased body parts.

"Preservation" refers to the use of chemical agents, alterations in environmental conditions or other means during processing to prevent or retard biological or physical deterioration of biological materials.

"Processing" refers to any activity performed on tissue, including preparation, preservation for storage and/or removal from storage to assure the quality and/or sterility of biological materials.

"Donor" refers to an individual from whom a biological material for future transplantation is obtained.

"Recipient" refers to an individual into whom a biological material is transplanted.

"Organ" refers to any part of the body exercising a specific function.

"Storage" refers to the miaintenance of biological materials for future use.

"Tissue" refers to a fuinctional group of cells.

"Transplantation" refers to the transfer of biological materials to a recipient.

"Solution" refers to a water-based medium capable of maintaining biological material viable under defined circumstances.

In one embodiment of a process in accordance with the present invention, blood vessels are removed from an animal or human, flushed and placed in a treatment or in a transport composition containing a culture media composition.

The treatment composition of the present invention contains polyethylene glycol (PEG) and an antioxidant, preferably glutathione (GSH). When the treatment composition is part of a transport solution, the transport solution composition can also include Normal Saline, lactated Ringer's solution, Plasmalyte and organ perfusates.

The PEG is contained in the tsport or treatment composition in an amount between about 0.1 and about 20% by weight, and more particularly between about 3 and 15% by weight, and most preferably about 10% by weight.

The GSH or other antioxidant is contained in the transport or treatment solution in an amount between about 0.1 and about 1000 micromolar, and more particularly in an amount between about I and 100 micromolar, and most preferably about 10 micromolar.

The vascular tissues in the PEG/GSH treatment solution are preferably contacted with the PEG/GSH solution for at least about 1 hour, and more preferably between about 1 and about 24 hours, and still more preferably between about 12 and about 16 hours, for example, at least about 12 hours, prior to cryopreservation. In embodiments of the present invention, it is preferred that the vascular tissues be maintained in the treatment composition for at least the 12 hours immediately prior to cryopreservation, i.e., that contact with treatment composition be maintained for as close to the moment of cryopreservation as possible. In other embodiments, however, it is sufficient that the vascular tissues be contacted with the treatment composition any time prior to cryopreservation.

The PEG/GSH treatment composition can also be employed post-tansport, but prior to cryopreservation, either as a stand alone treatment or during antibiotic exposure.

The veins or other vascular tissue in the transport or treatment composition are transported to a cryopreservation station where they are cryopreserved, after which they can be stored for an extended period of time until it is time for their transplantation into another animal or human.

EXAMPLES

Thirty inbred New Zealand White rabbits weighing 2.0 to 2.5 kg underwent right common carotid artery bypass grafting: Ten of the animals received fresh contralateral jugular veins from control rabbits (allogenic); ten animals received jugular veins that had been harvested, transported in culture media, cryopreserved and stored for six weeks (Comparative cryopreserved group); and ten received jugular veins in accordance with the present invention, the veins having been harvested, transported in culture media with 10% polyethylene glycol (PEG) and glutathione (GSH: 10 μM), cryopreserved and stored for 6 weeks (PEG/GSH group).

The animals were sacrificed with an overdose of barbiturates at 28 days after the operation and were harvested for morphology and planimetry. Animal care complied with the "Principles of Laboratory Animal Care" as formulated by the National Society for Medical Research and the Guide for the Care and Use of Laboratory Animals" issued by the National Institutes of Health. (U.S. Department of Health and Human Services, NIH Publication No. 80-23, revised 1985).

Anesthesia was induced and maintained with subcutaneously injected ketamine hydrochloride (60 mg/kg, Ketaset, Bristol Laboratories, Syracuse, N.Y.) and xylazine (6 mg/kg, Anased, Lloyd Laboratories, Shenandoah, Iowa). Antibiotic prophylaxis with 30,000 IU/kg of benzanthine and procaine penicillin (Durapen, Vedco Inc., Overland Park, Kans.) was given intramuscularly at the time of anesthesia. Surgery was performed using an operating microscope (JKH 1402, Edward Weck Inc., Research Triangle Park, N.C.) under sterile conditions. After exposure through a midline longitudinal neck incision, the left external jugular vein was identified, its branches were diathermied (heated with electromagnetic current) at a distance from the vein to minimize injury and were dissected out. This vein was kept moist in a heparinized Ringer's lactate solution (5 IU/ml, Heparin, Elkins-Sinn Inc., Cherry Hill, N.J.) for approximately 30 minutes while the right common carotid artery of a second recipient rabbit was anaesthetized and its right common carotid artery was dissected out.

Veins destined for cryopreservation were processed according to the protocol described below. The cryopreserved vein graft was thawed per a standard protocol, then inserted into the common carotid artery in a similar manner to the autologous vein graft after 6 weeks. Heparin (200 IU/kg) was administered intravenously. A proximal longitudinal arteriotomy was made and one end of the reversed jugular vein was anastomosed to the artery in an end-to-side manner using continuous 10-0 microvascular monofilament nylon suture (Ethilon, Ethicon Inc., Somerville, N.J.). The distal anastomosis was performed in a similar manner. Throughout the procedure, care was taken to avoid unnecessary instrumentation of the vein graft.

The right common carotid was ligated and divided between the two anastomoses with 4-0 silk sutures. The wound was closed in layers.

All jugular veins destined for cryopreservation were harvested using a sterile "no touch" technique. The veins were flushed with sterile Dulbecco's modified Eagle medium with 10% fetal calf serum and papaverine ($3 \times 10^{-4}$M), stored in culture media with or without 10%PEG and GSH (10 $\mu$M) and shipped on ice for cryopreservation within 24 hours of harvesting.

On arrival, the vein segments were cryopreserved in a solution containing 2.5% chondroitin sulfate in 1M dimethylsulfoxide and 10% fetal calf serum in HEPES buffered culture medium: vein segments were stored at $-96°$ C. in liquid nitrogen for 6 weeks in individual containers.

Veins were returned to the laboratory on dry ice and liquid nitrogen and stored in liquid nitrogen until surgery. Before implantation, the cryopreserved veins were thawed in the storage container in a water bath at 37° C. for 10 minutes. The vein segment was removed from the storage medium and placed in serial dilutions of solutions containing 0.5M, 0.25M and 0M mannitol and Dulbecco's modified Eagle medium with 10% fetal calf serum.

Following isolation and heparinization (200 IU/kg.I.V.), the control and experimental vein grfts were perfusion fixed in situ at 80 mm Hg with an initial infusion of Hanks Balanced Salt Solution (HBSS, Gibco Laboratories, Life Technologies Inc., Grand Island, N.Y.) followed by 2% glutaraldehyde made up in 0.1 M cacodylate buffer (pH 7.2) supplemented with 0M sucrose to give an osmolality of approximately 300 mOsm.

After 60 minutes the specimen was removed, immersed in glutaraldehyde fixative for a further 24 hours and then processed for light microscopy. Cross-sections from the mid-part of the graft were taken for processing. Following standard procedures, the specimens were stained with a modified Masson's trichrome and Verhoeff's elastin stain. The lumen, the intima and the media were defined and their dimensions (area and thickness) calculated by videomorphometry (Innovision 150, American Innovision Inc., San Diego, Calif.).

For scanning electron microscopy (SEM), mid-portion specimens of glutaraldehyde-fixed grafts were rinsed with the same buffer solution as described above, dehydrated in ascending concentrations of ethanol, transferred to acetone as an intermediate fluid, critical point dried in $CO_2$, mounted on specimen stubs and sputter-coated with gold-palladium according to standard techniques. All specimens were examined in a Philips 500 scanning electron microscope (N.V. Philips, Eindhoven, The Netherlands) at an accelerating voltage of 12 kV.

For transmission electron microscopy (TEM), representative sections from the mid-portion of the glutaraldehyde-fixed grafts were post-fixed for 1 hour at room temperature in 1% osmium-tetroxide dissolved in the same cacodylate buffer as used for the glutaraldehyde solution. After dehydration in ascending concentrations of ethanol, the specimens ware embedded in Epon 812 monomer. Polymerization was carried out overnight at 40° C. followed by 2 days at 60° C. Ultrathin sections were cut with a diamond knife on a Reichart ultramicrotome (Reichart Optische Werke AG, Vienna, Austria), contrasted with uranyl acetate and lead citrate and examined in a Philips 300 transmission electron microscope (N.V. Philips, Eindhoven, The Netherlands) operated at 40 kV.

Following determination of dimensions of each vein graft, a ratio of the intimal and medial areas was calculated (intimal ratio=intimal area/[intimal+medial areas]). Morphologic data are expressed as the mean±SEM and statistical comparisons are by Kruskal-Wallis ANOVA with Dunn's post hoc comparison testing. A p value less than 0.05 was regarded as significant.

All animals survived to harvest and all grafts were patent at harvest.

FIG. 1 shows a scanning electron micrograph, under an original magnification of 1250x, from a fresh 28 day allograft showing spindle shaped cells, termed neointimal cells (asterisks), covering most of the surface. The periphery of these neointimal cells have a ruffled border (arrowheads). Multiple adherent polymorphonucleocytes, macrophages (m) and platelets (arrows) can be seen. There are gaps in the luminal surface through which the subendothelial collagen can be seen in the center of the micrograph.

Figure 2:
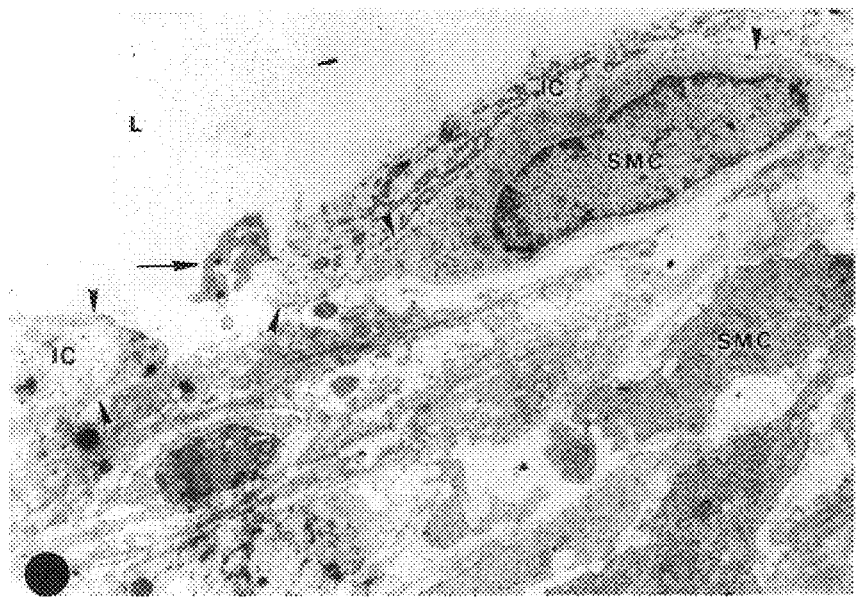
FIG. 2 is a transmission electron micrograph from a fresh allograft after 28 days in the arterial circulation at the surface.

FIG. 2 shows a transmission electron micrograph, under an original magnification of 5600x, from a fresh allograft after 28 days in the arterial circulation. At the surface, the spindle shaped neointimal cells (IC) noted in scanning electron microscopy are observed. Dense material (arrowheads) can be seen at the periphery of these cells compatible with contractile fibers. There is mural edema (asterisks) and variable collagen between the smooth muscle cells (SMC). The lumen L is also shown.

After 28 days, the intimal surface of the fresh allogenic vein grafts was covered by spindle-shaped cells (neointimal cells), which morphologically did not resemble endothelial cells (FIG. 1) in that they display a well formed rough endoplasmic reticulum with contractile material located at their peripheries, suggestive of intermediate phenotype smooth muscle cells (FIG. 2). The underlying smooth muscle cells had a cytoplasm filled predominantly with rough endoplasmic reticulum (FIG. 2). Cellular remnants and mural edema were noted in the wall. There were large amounts of collagen interspersed between the smooth muscles.

Figure 3:
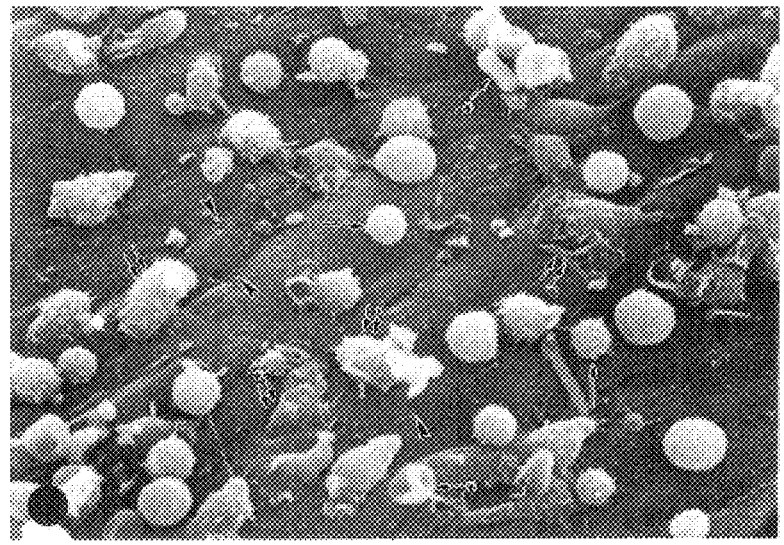
FIG. 3 is an electron micrograph from a cryopreserved graft after 28 days.

FIG. 3 shows a scanning electron micrograph, under an original magnification of 1250x from a cryopreserved 28 day graft showing numerous adherent blood cells. Polymorphonucleocytes (arrows) and macrophages (double arrows) are readily identifiable. One macrophage is shown about to enter a stoma (double arrow with asterisk). The endothelium appears intact with poorly visualized endothelial cell junctions (arrowheads). Red blood cells (single arrow with asterisk) can be seen.

Figure 4:
FIG. 4 is a transmission electron micrograph from a cryopreserved graft after 28 days in the arterial circulation.

FIG. 4 shows a transmission electron micrograph, under an original magnification of 4500x, from a cryopreserved graft after 28 days in the arterial circulation showing endothelial (E) and smooth muscle cells (SMC), both of which contain rough endoplasmic reticulum. The endoplasmic reticulum is abutting vesicles, suggesting a synthetic response to injury in these cells. Disintegrating remnants of cells and mural edema can also be seen deeper in the wall. On the surface, a macrophage (M) and a polymorphonucleocyte (PMN) are attached.

The 28 day old cryopreserved graft had an intact endothelium with poorly demarcated cell junctions on which were numerous adherent polymorphonucleocytes and macrophages (FIG. 3). Both the endothelial and underlying smooth muscle cells were filled with rough endoplasmic reticulum and vesicles (FIG. 4). The presence of such vesicles has been ascribed as a continuing cellular response to injury. Within the wall of these grafts, cellular remnants from dying and disintegrating cells and mural edema could be seen.

Figure 5:
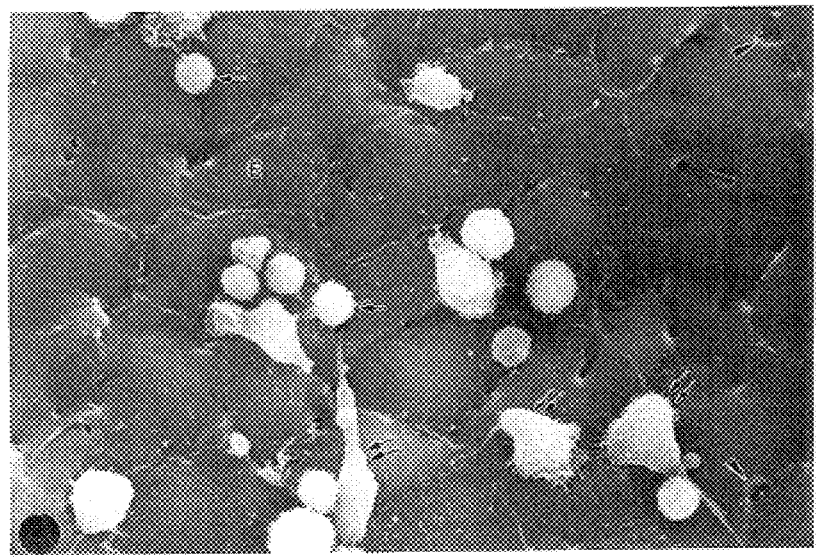
FIG. 5 is a scanning electron micrograph from a cryopreserved graft treated in accordance with the present invention after 28 days in the arterial circulation.

FIG. 5 shows a scanning electron micrograph, under an original magnification of 1250x, from a PEG/GSH treated 28 day cryopreserved graft showing intact endothelial cells (E) with stomata at the cell junctions (arrowheads), some attached polymorpho-nuclear granulocytes (small arrows) and macrophages (double arrows).

Figure 6:
FIG. 6 is a transmission electron micrograph from a cryopreserved graft treated in accordance with the present invention after 28 days in the arterial circulation.

FIG. 6 shows a transmission electron micrograph, under an original magnification of 1250x, from a PEG/GSH treated cryopreserved graft after 28 days in the arterial circulation showing intact unaltered endothelial cells (E) and underlying smooth muscle cells (SMC) with rough endoplasmic reticulum and vesicles suggesting a synthetic phenotype similar to that seen in the cryopreserved vein graft. A large macrophage (M) is seen deep in the intimal smooth muscle cell layers. Disintegrating smooth muscle cells and mural edema are also seen deeper in the wall but is not as extensive as that seen in the cryopreserved graft.

The PEG/GSH treated cryopreserved graft had an intact endothelial cell layer with the occasional adherent polymorphonucleocyte and macrophage (FIG. 5). The underlying intimal and medial smooth muscle cells were filled with rough endoplasmic reticulum similar to that seen in the cryopreserved vein graft (FIG. 6). Disintegrating smooth muscle cells and mural edema could be seen deeper in the wall although these were not as extensive as that seen in the cryopreserved graft.

Figure 7:
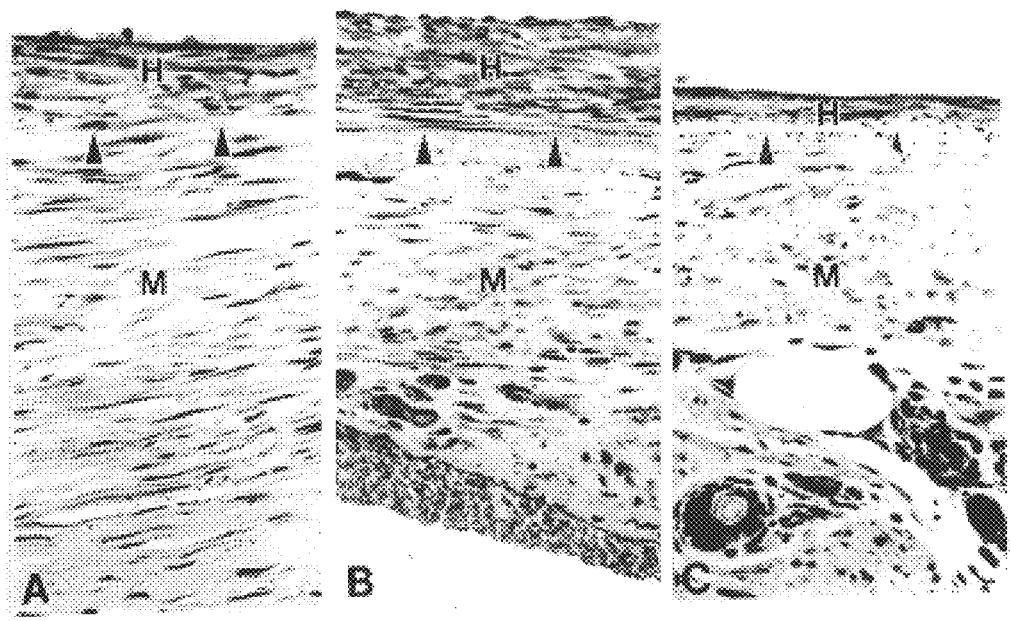
FIG. 7 is a composite photomicrograph showing cross-sections of the walls of fresh and cryopreserved and treated/cryopreserved in accordance with the present invention allogenic vein grafts at 28 days.

FIG. 7 is a composite photomicrograph, under an original magnification of 250x, showing cross-sections of the walls of fresh (A), cryopreserved (B), and PEG/OSH treated cryopreserved (C) allogenic vein grafts at 28 days.

At 28 days, the histological responses of the fresh and cryopreserved allogenic vein grafts were different (FIG. 7). At 28 days, the cryopreserved vein graft showed a 54% increase in overall mean intimal thickness (63±10 $\mu$m: p<0.05) but no change in overall mean medial thickness (125±9 $\mu$m: p=ns) compared to the fresh allograft (see Table I). The boundary between the intima (H) and the media (M) is indicated by arrowheads (FIG. 7).

Transport of the cryopreserved vessel in PEG/GSH resulted in the abolition of this increase in overall mean intimal thickness (41±$\mu$m: p<0.01) associated with cryopreservation without a change in overall mean medial thickness (119±13 $\mu$m: p<0.01) compared to the cryopreserved allograft (See Table 1 below).

Following cryopreservation and reimplantation into the donor animal, rabbit autologous vein grafts have been shown to have a smooth endothelial cell lining with intact cell junctions by 1, 2 and 3 months post-operatively. Using the composition of the present invention, cryopreserved allografts have a significantly improved luminal morphological appearance with far more endothelial cells and fewer neointimal cells than allograft controls. Treatment with the PEG/GSH containing composition prior to cryopreservation maintained the endothelial cell morphology similar to that reported for autologous vein grafts. The presence of an intact endothelium in a cryopreserved vein graft has previously been shown to correlate with normal prostacyclin production (see "Cryopreserved Venous Homografts as Vascular Conduits in Canine Carotid Arteries" by Showalter et al. in Surgery 106:652–659 (1989)) and the preservation of endothelial fibrinolytic activity (see "Venous Cryopreservation: Endothelial Fibronolytic Activity and Histology by Malone et al. in J Surg Res 29:209–222 (1980)).

In both the fresh and cryopreserved allografts there were many adherent platelets, polymorphonucleocytes and macrophages on the surface. In comparison, the addition of PEG/GSH demonstrated a markedly reduced number of adherent leukocytes.

Using the composition of the present invention, both polymorphonucleocytes and macrophages could be identified on the surface of all of the grafts. Macrophages were also noted within the intimal smooth muscle cell layers.

Compared to the fresh allograft, the cryopreserved allograft showed a 54% increase in overall mean intimal thickness but no change in overall mean medial thickness. Transport of the cryopreserved vessel in PEG/GSH resulted in the abolition of the increased intimal thickness associated with cryopreservation without a change in the mean medial response. A possible explanation for the decrease in the intimal response is that glutathione and PEG are both strong antioxidants and may have prevented oxidant-induced stress.

It is unlikely that the beneficial effect of PEG/GSH treatment prior to cryopreservation is due to an immunosuppressive effect of PEG for the following reasons: (1) Fresh allogeneic veins did not demonstrate the degree of intimal hyperplasia exhibited by cryopreserved allografts as demonstrated by the results in Table I; (2) Cryopreservation has been shown to have a mild immunosuppressive effect in allogeneic vein transplantation (see Angelli NP, Lupinetti FM, El Khatib et al., "Allograft Effects of Cryopreservation and Cyclosporine," Transplantation 52: 466–470 (1991)).

Little intimal development was seen in the fresh untreated control vein allografts at 28 days. However, following cryopreservation the intimal response increased dramatically. Treatment of the vein grafts with PEG/GSH for a minimum of 12 hrs prior to cryopreservation, prevented the enhanced intimal response seen in the cryopreserved vein grafts and resulted in dimensions of the intima comparable to the fresh allograft. This invention provides a significant improvement in the vasculopathy associated with cryopreserved allografts.

Cryopreserved vein grafts develop significant intimal hyperplasia compared to fresh allografts and this may point to an answer to the vexing question of why these grafts have such short in vivo patency. It is striking that treatment with PEG/GSH significantly reduces this vein graft intimal hyperplasia in comparison to that seen in untreated cryopreserved allografts. Furthermore, treatment with PEG/GSH resulted in better morphological preservation of endothelium as compared with both fresh and cryopreserved allograft explants. The use of a PEG/GSH treatment step to treat blood vessels prior to cryopreservation may be beneficial in clinical practice.

Table I

|  | Fresh | Cryopreserved | PEG/GSH | p-value |
|---|---|---|---|---|
| Lumen (mm$^2$) | 12.8 ± 0.5 | 14.5 ± 0.9 | 17.1 ± 2.1 | ns |
| Intima (mm$^2$) | 0.53 ± 0.04 | 0.84 ± 0.11* | 0.60 ± 0.07 | 0.03 |
| Media (mm$^2$) | 1.88 ± 0.23 | 1.78 ± 0.15 | 1.86 ± .031 | ns |
| Intimal ratio | 0.23 ± 0.02 | 0.32 ± 0.04 | 0.26 ± 0.02 | ns |

Table I lists the dimensional analysis for the experimental results including the areas of the lumen, intima and media from the midpart of the autologous, allogenic control, cryopreserved and GSH/PEG cryopreserved vein grafts at 28 days. The intimal ratio (intimal area/[intimal+medial areas]) is also presented. Values are the mean±SEM. Statistical comparisons were made using Kruskal-Wallis ANOVA with Dunn's post hoc comparison testing (*p<0.05) compared to cryopreserved grafts.

Although the above examples are described as having been conducted on rabbits, it is believed that the present invention is applicable to other animals, including mammals in general and humans in particular, and tissue engineered blood vessel-equivalents. Thus, the present invention is by no way limited to application to one particular animal, and instead wide applicability will be readily apparent to those of ordinary skill in the art.

While the present invention has been described in conjunction with the specific embodiments outlined above, it is evident that alternatives, modifications, and variations will be apparent to those skilled in the art. Accordingly, the preferred embodiments of the invention, as set forth above, are intended to be illustrative, not limiting. Various changes may be made without departing from the spirit and scope of the invention as defined in the following claims.

What is claimed is:

1. A method of treating vascular tissue prior to cryopreservation, storage and transplantation, comprising placing the vascular tissue in contact with a first composition containing polyethylene glycol and an antioxidant in amounts effective to inhibit cryopreservation-induced intimal hyperplasia in the vascular tissue upon transplantation, and placing the vascular tissue in contact with a different second composition for cryopreservation.

2. The method of claim 1, wherein the polyethylene glycol is present in the composition in a concentration of from about 0.1% to about 20% by weight.

3. The method of claim 2, wherein the polyethylene glycol is present in an amount between about 3% and about 15% by volume.

4. The method of claim 2, wherein the polyethylene glycol is present in an amount of about 10% by volume.

5. The method of claim 1, wherein the antioxidant is present in the first composition in a concentration between about 0.1 micromolar and about 1000 micromolar.

6. The method of claim 5, wherein the antioxidant is present in the first composition in a concentration between about 1 micromolar and about 300 micromolar.

7. The method of claim 6, wherein the antioxidant is present in the first composition in a concentration of about 10 micromolar.

8. The method of claim 1, wherein the antioxidant is glutathione.

9. The method of claim 8, wherein the polyethylene glycol is present in the first composition in a concentration of from about 0.1%, to about 20% and glutathione is present in the first composition in a concentration of from about 0.1 to 1000 micromolar.

10. The method of claim 9, wherein said polyethylene glycol is present in the first composition in an amount between about 3% and about 15% by volume and said glutathione is present in the first composition in a concentration of from about 1 to 300 micromolar.

11. The method of claim 10, wherein the amount of polyethylene glycol is about 10% and the amount of glutathione is about 10 micromolar.

12. The method of claim 1, further comprising cryopreserving vascular tissue after contacting with the first composition.

13. The method of claim 12, further comprising, after the step of cryopreserving, storing the vascular tissue in liquid nitrogen.

14. The method of claim 13, wherein the first composition is contacted with the vascular tissue for at least 12 hours.

15. The method of claim 14, wherein the first composition is contacted with the vascular tissue for at least 12 hours before said cryopreserving of vascular tissue is conducted.

16. The method of claim 1, wherein the vascular tissue comprises one or more artery segments.

17. The method of claim 16, further comprising cryopreserving the one or more artery segments after treatment with the first composition.

18. The method of claim 17, wherein the first composition is contacted with the one or more artery segments for at least 12 hours.

19. The method of claim 18, wherein the first composition is contacted with the one or more artery segments for at least 12 hours before said cryopreserving of the one or more artery segments is conducted.

20. A method of ameliorating the formation of intimal hyperplasia in vascular grafts, comprising contacting vascular tissue with a first composition comprising polyethylene glycol and glutathione; cryopreserving said vascular tissue with a different second composition; and transplanting the vascular tissue.

21. The method of claim 20, wherein the first composition is contacted with the vascular tissue for at least 12 hours before the cryopreserving of the vascular tissue is conducted.

22. The method of claim 20, wherein the vascular tissue comprises one or more vascularized organ segments.

23. The method of claim 22, wherein the one or more vascularized organ segments are selected from the group consisting of venous, arterial or vascularized organs.

24. A method, comprising:
   removing vascular tissue from a donor organism;
   contacting for at least about 12 hours the vascular tissue with a first composition comprising between about 5 to about 20% by weight of polyethylene glycol and between about 1 and 100 micromolar amount of glutathione;
   crygopreserving said vascular tissue with a different second composition; and
   transplanting the vascular tissue to an organism different from the donor organism.

25. The method of claim 1, wherein said second composition contains no polyethylene glycol.

26. The method of claim 25, wherein said second composition contains no glutathione.

27. The method of claim 20, wherein said second composition contains no polyethylene glycol.

28. The method of claim 27, wherein said second composition contains no glutathione.

29. The method of claim 24, wherein said second composition contains no polyethylene glycol.

30. The method of claim 29, wherein said second composition contains no glutathione.

* * * * *